United States Patent
Srinivas et al.

(10) Patent No.: US 6,649,791 B2
(45) Date of Patent: Nov. 18, 2003

(54) PROCESS FOR THE PREPARATION OF AN AROMATIC CARBOXYLIC ACID

(75) Inventors: Darbha Srinivas, Pune (IN); Suhas Arunkumar Chavan, Pune (IN); Paul Ratnasamy, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/912,456

(22) Filed: Jun. 28, 2001

(65) Prior Publication Data

US 2003/0050504 A1 Mar. 13, 2003

(51) Int. Cl.⁷ .................. C07C 51/255; B01J 23/32
(52) U.S. Cl. .................. 562/416; 562/412; 502/324
(58) Field of Search .................. 562/412, 414, 562/416; 502/324

(56) References Cited

U.S. PATENT DOCUMENTS 2,833,816 A * 5/1958 Saffer et al. ................ 562/416

FOREIGN PATENT DOCUMENTS

EP 0618186 10/1994

OTHER PUBLICATIONS

Rouchard et al, Oxydation du Para–Xylene Liquide catalysee par les Zeolithes Charge D'elements de Transition, 1968,Bulletin de la Societe Chimique Belges, 77, pp. 537–542.*

Tsuruya et al, Oxidation of Benzyl Alcohol over Co(II)NaY Zeolites, 1980, Journal of Catalysis, 64, pp. 260–271.*

Chavan et al, Journal of Molecular Catalysis A, Formation and Role of Cobalt and Manganese Cluster Complexes in the Oxidation of p–Xylene, 2000, 161(1–2), pp. 49–64. Abstract Only.*

Chavan, S.A., et al. "A novel, zeolite–encapsulated u3–oxo Co/Mn cluster catalyst for oxidation of para–xylene . . . " Chemical Communication, vol. 12, (2001) pp 1124–1125.

* cited by examiner

Primary Examiner—Johann Richter
Assistant Examiner—Paul A. Zucker
(74) Attorney, Agent, or Firm—Ladas and Parry

(57) ABSTRACT

The present invention relates to the preparation of an aromatic carboxylic acid by contacting an alkyl aromatic compound with an oxygen containing gas in the presence of an encapsulated oxo-bridged organometallic cluster catalyst.

8 Claims, No Drawings

PROCESS FOR THE PREPARATION OF AN AROMATIC CARBOXYLIC ACID

FIELD OF THE INVENTION

The present invention relates to a process for the preparation of an aromatic carboxylic acid. More particularly, the present invention relates to a process for the preparation of an aromatic carboxylic acid of the general formula

R—COOH wherein R comprises an aryl group having 1 to 3 benzene rings, or a substituted aryl group. Still more particularly, it relates to the preparation of aromatic carboxylic acids by oxidation of alkyl aromatic compounds having a general formula $R_1$—$R_2$ wherein $R_1$=alkyl or substituted alkyl having 1 to 3 carbon atoms, and $R_2$=aryl having 1 to 3 benzene rings, using solid catalysts containing organometallic cluster complexes of cobalt and manganese.

BACKGROUND OF THE INVENTION

Aromatic carboxylic acids such as benzoic acid, phthalic acid, terephthalic acid, trimethyl benzoic acids, naphthalene dicarboxylic acids and the like are used widely as intermediates in the chemical industry. They are usually prepared from the corresponding alkyl aromatic compounds by oxidation with air in the presence of liquid phase, homogeneous catalysts like cobalt acetate, manganese acetate etc. Terephthalic acid, for example, is prepared, as described in U.S. Pat. No. 2,833,816 issued to Mid Century Coloration in 1958, by the oxidation of para-xylene by air in acetic acid solvent, at around 200° C. and 200 psig pressure, in the presence of homogeneous, liquid phase catalysts comprising of cobalt, manganese and bromine. Various modifications and improvements of this process are utilised for the manufacture of terephthalic and many other aromatic carboxylic acids. These processes are described in U.S. Pat. Nos. 5,693,856; 3,562,318A; 5,760,288; 6,160,159; 4,329,493; 4,593,122; 4,827,025; 4,835,307; 5,087,741; 5,112,992; and EP 0 754,673 A. Comprehensive reviews of the oxidation of alkyl aromatic compounds to aromatic carboxylic acids are available by Suresh et al in Industrial Engineering Chemistry Research, volume 39, pages 3958–3997, year 2000 and W. Partenheimer in Catalysis Today, volume 23, pages 69–158, year 1995. Phthalic acid is manufactured by the aerial oxidation of ortho-xylene in the vapor phase over vanadia-based catalysts. In the oxidation of para-xylene to terephthalic acid, for example, the process begins with hydrogen atom extraction from a methyl group by the bromine atom. The resultant benzyl radical adds to $O_2$ and proceeds through the hydroperoxide to para-tolyl alcohol, para-tolyl aldehyde and para-toluic acid. Hydrogen atom abstraction from the methyl group of toluic acid generates a secondary benzyl radical, which follows the same pathway to yield, eventually, terephthalic acid.

There are many improvements that are desirable in the presently used homogeneous, liquid phase processes for the manufacture of aromatic carboxylic acids; (1) Replacement of the homogeneous by solid heterogeneous catalysts, (2) replacement of the corrosive bromine promoters which require the use of expensive titanium steel, by non-corrosive compounds, (3) elimination or reduction of the significant acetic acid oxidation to CO and carbon dioxide (5–10 wt. % of the carboxylic acid); this can, perhaps, be achieved by the use of more efficient radical promoters which allow oxidizer temperatures to be lowered without reducing reaction rates, and (4) lowering of the concentration, in the reaction product, of intermediates which are difficult to be removed from the final, aromatic carboxylic acid product: 4-carboxy benzaldehyde is a typical example of such an intermediate which necessitates elaborate hydrogenation and recrystallisation procedures in the manufacture of purified terephthalic acid required for the polyester industry.

Jacob et al in the journal Applied Catalysis A: General, volume 182, year 1999, pages 91–96 described the aerial oxidation of para-xylene over zeolite-encapsulated salen, saltin and salcyhexen complexes of cobalt or manganese in the absence of added halogen promoters and using tertiary butyl hydroperoxide, instead of bromide ions, as the initiator at low temperatures. Significant conversion levels of para-xylene (upto 50–60%) were attained. However, the main product was para toluic acid. The yields of terephthalic acid were negligible. The feasibility of using a solid, non-Br-containing catalyst in the absence of any solvent including acetic acid for the para-xylene oxidation to toluic acid, which is the first stage in the oxidation of para-xylene to terephthalic acid, was claimed to be established.

In prior art processes for the manufacture of aromatic carboxylic acid from alkyl aromatic compounds, the alkyl aromatic compound is dissolved in acetic acid along with the homogeneous catalysts, usually the acetates of cobalt and manganese, and oxidized by an oxygen containing gas, usually air or oxygen, in the presence of a promoter like NaBr or HBr at temperatures around 200° C. and pressures of about 200 psig. Other metal acetates have also been used. U.S. Pat. No. 4,786,753, for example teaches the use of nickel, manganese and zirconium acetates in place of the acetates of cobalt and manganese. The commercial processes have been optimized to the point where typical crude aromatic acid yield is around 96–98% weight. However, as mentioned herein before, there is scope for improvement in the practice of the process one of them being the replacement of the homogeneous catalysts by solid catalysts since the latter can be more easily separated from the reaction products. In the investigations leading to the present invention, it was found that when complexes of cobalt, manganese, nickel, zirconium or any of their combinations were supported or encapsulated or grafted in solid supports, the yields of the aromatic carboxylic acids were always low in accord with the findings of Jacob et al published earlier and mentioned herein above. Hence, the prior art catalysts, like the acetates of cobalt, manganese, nickel or zirconium, while active in the homogeneous oxidation of alkyl aromatic compounds are not sufficiently active in the solid state. It is a surprising discovery of the present invention that when the solid catalyst contains certain organometallic cluster complexes of cobalt and manganese wherein each molecule of the cluster complex contains both cobalt and manganese, then their activity in the oxidation of alkyl aromatic compounds to aromatic carboxylic acids is enhanced significantly. These novel solid catalysts while retaining all the advantages of the homogeneous catalysts, like high yields of the desired aromatic carboxylic acids in the range of 96 to 98% weight, are easily separable from the reaction products by simple filtration processes, thereby not only avoiding the tedious process of catalyst recovery characteristic of prior art processes, but also eliminating the presence of toxic elements, like cobalt, manganese, nickel etc., in the waste effluent from the process. Processes utilizing these novel solid catalysts are, hence, environmentally more beneficial. Representative of the organometallic cluster complexes of cobalt and manganese of the present invention are $CoMn_2(O)(CH_3COO)_6$, $Co_2Mn(O)(CH_3COO)_6$, $CoMn_2(O)(CH_3COO)_y(pyridine)_z$, $Co_2Mn(O)(CH_3COO)_y(pyridine)_z$, where y+z=9, etc. It was also found that the organic ligands in the above mentioned organometallic cluster complex namely the acetate and pyridine ligands, can be replaced by other suitable organic moieties. The critical active site ensemble responsible for the high yields of aromatic carboxylic acids in the oxidation of the alkyl aromatic compounds was the heterometallic cluster complex containing both cobalt and manganese. While the exact origin of this enhancement effect is not known in detail, it is believed that multimetallic clusters of transition metal ions are better able to activate dioxygen, $O_2$, than monometallic and monomeric ions. The common prevalence of such heteronuclear multimetallic clusters in the $O_2$ activating enzymatic oxygenase catalyst systems supports such a suggestion. Processes for the manufacture of aromatic carboxylic acids using solid catalysts with high, almost complete, conversion of the alkyl aromatic compound and high yields of the aromatic carboxylic acid are continually sought.

OBJECTS OF THE INVENTION

It is therefore one of the objects of the present invention to provide a process for production of aromatic carboxylic acids having high conversions and high yields.

Another object is to provide a process for the production of aromatic carboxylic acids using solid catalysts.

Still another object of the present invention is to provide a process for the production of terephthalic acid using solid catalysts consisting of organometallic clusters of cobalt and manganese.

SUMMARY OF THE INVENTION

In the investigations leading to the present invention, it was found that when complexes of cobalt, manganese, nickel, zirconium or any of their combinations were supported or encapsulated or grafted in solid supports, the yields of the aromatic carboxylic acids were always low in accord with the findings of Jacob et al published earlier and mentioned herein above. Hence, the prior art catalysts, like the acetates of cobalt, manganese, nickel or zirconium, while active in the homogeneous oxidation of alkyl aromatic compounds are not sufficiently active in the solid state. It is a surprising discovery of the present invention that when the solid catalyst contains certain organometallic cluster complexes of cobalt and manganese wherein each molecule of the cluster complex contains both cobalt and manganese, then their activity in the oxidation of alkyl aromatic compounds to aromatic carboxylic acids is enhanced significantly. These novel solid catalysts while retaining all the advantages of the homogeneous catalysts, like yields of the desired aromatic carboxylic acids in the range of 96 to 98% weight, could be easily separated from the reaction products by simple filtration processes, thereby not only avoiding the tedious process of catalyst recovery characteristic of prior art processes, but also eliminating the presence of toxic elements, like cobalt, manganese, nickel etc., in the waste effluent from the process. Processes utilizing these novel solid catalysts are, hence, environmentally more beneficial. Representative of the organometallic cluster complexes of cobalt and manganese of the present invention are $CoMn_2(O)(CH_3COO)_6$, $Co_2Mn(O)(CH_3COO)_6$, $CoMn_2(O)(CH_3COO)_y(pyridine)_z$, $Co_2Mn(O)(CH_3COO)_y(pyridine)_z$, where y+z=9, etc. It was also found that the organic ligands in the above mentioned organometallic cluster complex, namely the acetate and pyridine ligands, can be replaced by other suitable organic moieties. The critical active site ensemble responsible for the high yields of aromatic carboxylic acids in the oxidation of the all aromatic compounds was the heterometallic cluster complex containing both cobalt and manganese. While the exact origin of this enhancement effect is not known in detail, it is believed that multimetallic clusters of transition metal ions are better able to activate dioxygen, $O_2$, than monometallic and monomeric ions. The common prevalence of such heteronuclear, multimetallic clusters in the $O_2$ activating enzymatic oxygenase catalyst systems supports such a suggestion.

Accordingly the present invention relates to a process for the preparation of an aromatic carboxylic acid which comprises oxidizing an alkyl aromatic compound by contacting the said alkyl aromatic compound with an oxygen containing gas at a temperature in the range of 80 to 250° C., in the presence of a solid catalyst for a period of 45 to 240 minutes at a pressure ranging between 200 to 550 psig, and recovering the desired product.

In one embodiment of the invention, the aromatic acid has the general formula

R—COOH wherein R is an aryl group having 1 to 3 benzene rings, or a substituted aryl group.

In another embodiment of the invention, the alkyl aromatic compound has the general formula $R_1$—$R_2$ wherein $R_1$=alkyl or substituted alkyl having 1 to 3 carbons, and $R_2$=aryl having 1 to 3 benzene rings.

In another embodiment of the invention, the solid catalyst used is of the general formula $[M_xM'_{x'}(O)(RCOO)_nL_{n'}]Y_{n''}$ wherein M and M' are cobalt and manganese ions, x and x' are each between 0 to 3, R is selected from the group consisting of an alkyl group containing 1 to 5 carbon atoms, an aryl group with 1 to 3 benzene rings, substituted alkyl and aryl group, n is between 3 to 6, L is selected from the group consisting of RCOO, pyridine, nitrogen containing organic bases, $H_2O$ and organic solvent and any like ligand, Y is a halide ion, $ClO_4^-$, $BF_4^-$, $PF_6^-$, $BrO_3^-$ or any like ion, n' and n'' are each between 0 to 3.

In a further embodiment of the invention, the oxygen containing gas is selected from the group consisting of pure oxygen, air and a mixture of gases containing oxygen.

In yet another embodiment of the invention, the desired product is recovered by condensation and distillation.

In still another embodiment the solid catalyst is of general formula $[M_xM'_{x'}(O)(RCOO)_nL_{n'}]Y_{n''}$ wherein M and M' are transition metal ions and more specifically cobalt and manganese ions, x and x' may vary from 0 to 3, R may be an alkyl group containing 1 to 5 carbon atoms or an aryl group with 1 to 3 benzene rings or substituted alkyl or aryl group, n may vary from 3 to 6, L may be RCOO, pyridine, nitrogen containing organic bases, $H_2O$, organic solvent or any like ligand, Y may be a halide ion, $ClO_4^-$, $BF_4^-$, $PF_6^-$, $BrO_3^-$ or any like ion, n' and n'' may vary from 0 to 3 and characterized by Table 1

TABLE 1

Characterization data of solid Co/Mn cluster complex

| | |
|---|---|
| FT-IR bands (in cm$^{-1}$; nujol mull) | 2924, 1624, 1458, 1221, 680 (for acetato group) |
| | 1545, 1489, 790 (for pyridine) |
| Diffuse reflectance | |
| UV-Visible bands (in nm) | An intense band at 254 nm |
| ESR | At signal at g = 2.023 |

DETAILED DESCRIPTION OF THE INVENTION

The method of the present invention utilises a solid oxidation catalyst which has been found to be particularly effective for oxidation of aromatic aryl groups to the carboxyl groups in high yields. The catalyst system is a solid catalyst containing an organometallic complex of cobalt and manganese. Examples of such solid catalysts include micro and mesoporous material like, aluminosilicate zeolites, aluminophosphates, carbon molecular sieves, silica and the like, containing an organometallic complex wherein the chemical composition of each molecule of the organometallic complex includes at least one atom of both cobalt and manganese.

An alkyl aromatic compound is oxidised by contacting with an oxygen-containing gas at a temperature in the range of 80 to 250° C., in the presence of a solid catalyst for a period of 45 to 240 minutes at a pressure ranging between 200 to 550 psig. The product is recovered by conventional methods such as condensation and distillation.

The aromatic acid is preferably of the general formula R—COOH, where R is an aryl group having 1 to 3 benzene rings, or a substituted aryl group.

The alkyl aromatic compound may also have the general formula $R_1$—$R_2$ wherein $R_1$=alkyl or substituted alkyl having 1 to 3 carbons, and $R_2$=aryl having 1 to 3 benzene rings.

The catalyst is of the general formula $[M_xM'_{x'}(O)(RCOO)_nL_{n'}]Y_{n''}$ where M and M' are transition metal ions preferably cobalt or manganese ions, x and x' may vary from 0 to 3, R may be an alkyl group containing 1 to 5 carbon atoms or an aryl group with 1 to 3 benzene rings or substituted alkyl or aryl group, n may vary from 3 to 6, L, may be RCOO, pyridine, nitrogen containing organic bases, $H_2O$, organic solvent or any like ligand, Y may be a halide ion, $ClO_4^-$, $BF_4^-$, $PF_6^-$, $BrO_3^-$ or any like ion, n' and n" may vary from 0 to 3.

Table 1 below gives the characterisation data of the solid Co/Mn cluster complexes.

TABLE 1

Characterization data of solid Co/Mn cluster complex

| | |
|---|---|
| FT-IR bands (in cm$^{-1}$; nujol mull) | 2924, 1624, 1458, 1221, 680 (when L is RCOO) |
| | 1545, 1489, 790 (when L is pyridine) |
| Diffuse reflectance | |
| UV-Visible bands (in nm) | An intense band at 254 nm |
| ESR | At signal at g = 2.023 |

Copending U.S. patent application Ser. No. 09/894,997 (NF 270/01) describes the catalyst system used in the instant invention and a process for the preparation thereof.

The oxygen containing gas may be pure oxygen, air or mixture of gases containing oxygen and is preferably air.

Oxidation of the alkyl aromatic compound to the aromatic carboxylic acid is done in the presence of an oxygen containing gas and a solid catalyst containing an organometallic cluster complex of cobalt and manganese. The separation of the solid crystals of the aromatic carboxylic acid from the reaction product and isolating from the solid crystals of aromatic carboxylic acid, an aromatic carboxylic acid having a purity greater than 99% by weight.

The solid catalyst has an organometallic cluster complex with at least one atom of cobalt and one atom of manganese in each molecule of the cluster complex and can be separated from the solid crystals of the product from the reaction mixture.

This invention is illustrated by the following examples, which are illustrative only, and should not be construed to limit the scope of the present invention.

EXAMPLE-1

This example illustrates the preparation of the organometallic catalyst (designated as catalyst system (10)). Mixed metal Co—Mn(II) exchanged zeolite-HY was prepared by ion-exchange method, in which zeolite HY (7 g) was interacted with 4.3 g of $Mn(CH_3COO)_2.4H_2O$ and 1.43 g of $Co(CH_3COO)_2.4H_2O$ dissolved in 100 ml distilled water at 60° C. with constant stirring. The solid product was then washed thoroughly with water (500 ml) and dried at 100° C. CoMnY (1.5 g) was taken in 15 ml glacial acetic acid and to this was added pyridine (3 ml), NaBr (0.5 g) and aq. $H_2O_2$ (50%, 10 ml) and distilled water (5 ml). The reaction mixture was stirred while passing air, for 2 h, at 25° C. The brown solid zeolite (CoMn-cluster complex encapsulated in zeolite-Y; was then filtered and dried at 25° C. under vacuum.

EXAMPLE-2

Prior Art Catalyst Preparation

Prior art catalysts (1) and (2) were the acetates of manganese and cobalt, $Mn(CH_3COO)_2.4H_2O$ and $Co(CH_3COO)_2.4H_2O$, respectively, obtained from Aldrich Co., They were used as received. Prior art catalyst (3) was a mixture of $Mn(CH_3COO)_2.4H_2O$ and $Co(CH_3COO)_2.4H_2O$ in the mmole ratio of 0.35:1.03. Prior art catalyst (4) was a mixture of $Mn(CH_3COO)_2.4H_2O$ and $Co(CH_3COO)_2.4H_2O$ in the mmole ratio of 0.7:0.7. The mixture of $Mn(CH_3COO)_2.4H_2O$ and $Co(CH_3COO)_2.4H_2O$ in the mmole ratio of 1.03:0.35 mmol is designated as prior art catalyst system (5). The catalyst of the prior art, designated as catalyst (6), was prepared as follows: To a solution of absolute alcohol (20 ml) containing $Mn(CH_3COO).4H_2O$ (2.5 g), glacial acetic acid (12 ml) and pyridine (3 ml) were added. The reaction was stirred until a colourless, homogeneous solution was obtained. Then, an ethanolic solution (10 ml) of N-n-$Bu_4MnO_4$ (1.14 g) was added in small amounts over a period of 45 min and the resultant brown solution was stirred for another 30 min. To that, 0.695 g of $NaClO_4$ was added in small amounts while stirring and the stirring was continued for another 15 min after complete addition of $NaClO_4$. A brown crystalline product was obtained in 2–3 days on slow evaporation at 23° C. The product was purified by washing with ethanol and drying in vacuum. A prior art catalyst, designated as catalyst (7) was prepared as follows: $Co(CH_3COO)_2.4H_2O$ (1.25 g) taken in a solution of glacial acetic acid (12.5) and pyridine (0.4 g) were heated to 50° C. while stirring. To this purple coloured reaction mixture a freshly prepared peracetic acid (obtained by stirring a solution of glacial acetic acid (0.4 g) and 30% $H_2O_2$ (0.7 g)) was added drop-wise over a period of 30 min while stirring. The colour of the resultant solution was dark brown. Then, 3 ml of distilled water was added and the mixture was refluxed for 1 h at 80° C. It was then allowed to cool to 25° C. and a solution of $NaClO_4$ (0.4 g) in 20 ml distilled water was added. The resultant solution was stirred briefly and allowed to stand for a week at temperatures below 5° C. to obtain Catalyst (7) as a microcrystalline product.

A catalyst of the prior art, designated as catalyst (8), was prepared as follows: To a solution of ethanol (25 g) and glacial acetic acid (4.2 g) was added manganic ante (2.7 g) and stirred for 5–10 min till all the manganic acetate was dissolved. The brown solution was then filtered and to it was added $Co(CH_3COO)_2.4H_2O$ (2.5 g) in 4 g of hot pyridine with constant stirring. The resultant solution was allowed to stand. Shiny black crystals (Catalyst (8), a mixed cluster complex of cobalt and manganese) were obtained in 10 days. They were filtered, washed with ethanol and dried in vacuum. A catalyst of the prior art, designated as catalyst (9), was prepared as follows: Mn(II) exchanged zeolite-HY was prepared by ion-exchange method, in which zeolite HY (7 g) was interacted with 4.3 g of $Mn(CH_3COO)_2.4H_2O$ dissolved in 100 ml distilled water at 60° C. with constant stirring. The solid product was then washed thoroughly with water (500 ml) and dried at 100° C. MnY, thus obtained, was used in the preparation of Catalyst (9). In a typical preparation of Catalyst (9), MnY(1.5 g) was taken in glacial acetic acid (15 ml) and to it psig added pyridine (3 ml), NaBr (0.5 g) and aq. $H_2O_2$ (50%, 10 ml) and distilled water (5 ml). The reaction mixture was stirred while passing air, for 2 h, at 25° C. The brown solid zeolite ($Mn_3$ cluster encapsulated in zeolite-Y; Catalyst System (9)) was then filtered and dried at 25° C. under vacuum. A prior art catalyst, designated as catalyst (11), was prepared as follows: Co(II) exchanged zeolite-HY was prepared by the ion-exchange method, in which zeolite HY(7 g) was interacted with 4.3 g of $Co(CH_3COO)_2.4H_2O$ dissolved in 100 ml distilled water at 60° C. with constant stirring. The solid product was then washed thoroughly with water (500 ml) and dried at 100° C. CoY, thus obtained, was used in the preparation of Catalyst System (11). In a typical preparation of Catalyst System (11), CoY(1.5 g) was taken in 15 ml glacial acetic acid and to it was added pyridine (3 ml), NaBr(0.5 g), aq. $H_2O_2$ (50%, 10 ml) and distilled water (5 ml). The reaction mixture was stirred while passing air, for 2 h, at 25° C. The brown solid zeolite ($Co_3$ cluster encapsulated in zeolite-Y, Catalyst System (11)) was then filtered and dried at 25° C. under vacuum.

EXAMPLE 3

This example illustrates the procedure for the oxidation of para-xylene. The experiments were conducted in a closed titanium-lined pressure reactor (Parr 4843). In a typical catalysis experiment 2 ml of para-xylene, 38 ml of acetic aid, 5.6 ml water and 0.0865 g of NaBr and 1% weight (of para-xylene) of catalyst was taken. The reactions were conducted at 200° C. and 200 to 550 psig pressure for different time durations (45 min–4 h). At the end of the reaction, the reactor was cooled to 23° C. The liquid products (para-tolyl alcohol (A), para tolyl aldehyde (B), para-toluic acid (C)) and unreacted para-xylene were analysed by gas chromatography (Shimadzu GC 14 B SE-30 S.S. packed column). The reaction mixture was then distilled under vacuum to remove acetic acid, water, unreacted para--xylene if any, and liquid products (A and B). The solid mass obtained was washed repeatedly with hot water. The solid products (para-toluic acid (C), 4-carboxybenzaldehyde (E), terephthalic acid (F) and benzoic acid (G)) were taken in 15 ml water and 2M NaOH solution was added drop-wise till the solids dissolved. The pH of the solution was maintained at around 7. The produces was analyzed by HPLC (Shimadzu C-R4A Chromatopac; C18 column).

EXAMPLE-4

Comparative

This example illustrates the preparation of terephthalic acid from para xylene by the process of the present invention. Comparative data with prior art catalysts are also given. The oxidation reactions were carried out as described in Example-3 using catalysts described in Examples 1 and 2. The reactions were carried out at 200° C. and 550 psig pressure for 2 hours 163 mmole of para-xylene, 0.85 mmole of NaBr. 311 mmole of $H_2O$ and 639 mmole of acetic acid and air formed the reaction mixture along with the catalyst. In Table-2, products A–F, given in % by weight, correspond to para-tolyl alcohol (A), para-tolyl aldehyde (B), para-toluic acid (C), 4-carboxybenzaldehyde (D), terephthalic acid (E) and benzoic acid (F), respectively

TABLE 2

| | Preparation of Terephthalic Acid | | | | | | |
|---|---|---|---|---|---|---|---|
| Catalyst | Conv. % wt | A | B | C | D | E | F |
| 1 | 99 | — | — | 7.3 | 1.0 | 91.7 | 0.02 |
| 2 | 100 | — | — | 0.2 | 0.1 | 98.7 | 1.0 |
| 3 | 100 | — | — | 0.7 | 1.4 | 97.9 | 0.01 |
| 4 | 100 | — | — | 0.36 | 0.03 | 99.6 | 0.01 |
| 5 | 100 | — | — | 0.44 | 0.05 | 99.5 | 0.01 |
| 6 | 100 | — | — | 1.6 | 0.1 | 98.2 | 0.1 |
| 7 | 100 | — | 42.5 | 26.0 | 11.7 | 19.5 | 0.3 |
| 8 | 100 | — | — | 0.8 | 0.1 | 99.0 | 0.1 |
| 9 | 80.4 (4 h) | — | 37.8 | 30.8 | 1.7 | 29.7 | — |
| 10 | 100 (4 h) | — | — | 0.6 | 0.01 | 99.4 | — |
| 11 | 69.9 (4 h) | — | 28.4 | 49.5 | 7.7 | 12.7 | 1.7 |

The process described above has the combined unique advantage of complete conversion of para-xylene accompanied by the low concentration of 4-carboxy benzaldehyde, a key troublesome impurity in purified terephthalic acid, over the solid catalysts of the process of the present invention, namely catalyst (10) along with recyclability of the catalyst system.

Advantages of the Invention

1. The activity of the catalyst in oxidation of alkylaromatic compounds is enhanced significantly due to the presence of organometallic cluster complexes of both cobalt and manganese in the solid catalyst.

2. The solid catalyst used retains the advantages of homogeneous catalysts used in the prior art while at the same time being easily recoverably by simple filtration thus enabling easy recovery of the desired product.

3. The process of the invention is environmentally friendly, since toxic elements such as cobalt or manganese or nickel are absent from the effluent.

4. The yield of the process is high.

We claim:

1. A process for the preparation of an aromatic carboxylic acid which comprises oxidizing an alkyl aromatic compound by contacting the alkyl aromatic compound with an oxygen-containing gas at a temperature in the range of 80 to 250° C., in the presence of a solid catalyst of the formula $[M_xM'_{x'}(O)(RCOO)_nL_{n'}]Y_{n''}$ wherein M and M' are cobalt and manganese ions, x and x' are each between 0 to 3, with the proviso that only one of x and x' are 0, R is selected from the group consisting of an alkyl group containing 1 to 5 carbon atoms, an aryl group with 1 to 3 benzene rings, substituted alkyl and aryl group; n is between 3 to 6, L is selected from the group consisting of RCOO, pyridine, nitrogen containing organic bases, $H_2O$ and organic solvent, Y is selected from the group consisting of a halide ion, $ClO_4^-$, $BF_4^-$, $PF_6^-$, $BrO_3^-$, n' and n" are each between 0 to 3, for a period of 45 to 240 minutes at a pressure ranging between 200 to 550 psig, and recovering the desired product.

2. The process as claimed in claim 1 wherein the aromatic carboxylic acid prepared is of the formula R—COOH wherein R is an aryl group having 1 to 3 benzene rings, or a substituted aryl group.

3. The process as claimed in claim 1 wherein the alkyl aromatic compound used is of the formula $R_1$—$R_2$ wherein $R_1$ is alkyl or substituted alkyl having 1 to 3 carbons, and $R_2$ is aryl having 1 to 3 benzene rings.

4. The process as claimed in claim 1 wherein the solid catalyst used has the characteristics provided in Table 1 below:

TABLE 1

| Characterization data of solid Co/Mn cluster complex | |
|---|---|
| FT-IR bands (in $cm^{-1}$; nujol mull) | 2924, 1624, 1458, 1221, 680 (when L is RCOO) 1545, 1489, 790 (when L is pyridine) |
| Diffuse reflectance UV-Visible band (in nm) | An intense band at 254 nm |
| ESR | At signal at g = 2.023. |

5. The process as claimed in claim 1 wherein the catalyst is selected from the group consisting of $CoMn_2(O)(CH_3COO)_6$, $Co_2Mn(O)(CH_3COO)_6$, $CoMn_2(O)(CH_3COO)_y(pyridine)_z$, and $Co_2Mn(O)(CH_3COO)_y(pyridine)_z$ where y+z=9.

6. The process as claimed in claim 1 wherein the oxygen containing gas is selected from the group consisting of pure oxygen, air and a mixture of gases containing oxygen.

7. The process as claimed in claim 6 wherein the oxygen containing gas is air.

8. The process as claimed in claim 1 wherein the desired product is recovered by condensation and distillation.

* * * * *